United States Patent [19]

Westbrook et al.

[11] Patent Number: 5,060,681

[45] Date of Patent: Oct. 29, 1991

[54] DENTAL FLOSSING DEVICE

[75] Inventors: Robert S. Westbrook, 1582 Response Rd., #3056, Sacramento, Calif. 95815; Robin L. Hibbard, Davis, Calif.; Robert D. Davis, Davis, Calif.; Erik S. Drews, Davis, Calif.; Jerald M. Henderson, Davis, Calif.

[73] Assignee: Robert S. Westbrook, Sacramento, Calif.

[21] Appl. No.: 632,829

[22] Filed: Dec. 24, 1990

[51] Int. Cl.[5] .............................................. A61C 15/00

[52] U.S. Cl. .................................... 132/325; 132/323; 132/324

[58] Field of Search ........................ 132/323, 324, 325

[56] References Cited

U.S. PATENT DOCUMENTS

| | | | |
|---|---|---|---|
| 3,340,881 | 9/1964 | Cowan | 132/325 |
| 3,592,203 | 7/1971 | Johnson | 132/323 |
| 3,746,017 | 7/1973 | Casselman | 132/325 |
| 3,861,406 | 1/1975 | Stitt | 132/325 |

*Primary Examiner*—John J. Wilson

*Assistant Examiner*—Cindy A. Cherichetti

*Attorney, Agent, or Firm*—Lothrop & West

[57] ABSTRACT

An elongated handle with an internal supply of fresh dental floss and a flossing head including a fork provides oral hygiene. A fresh section of floss is advanced by a one-touch arrangement which concurrently relegates spent floss to a separate take-up reel. The fresh floss spanning the tines of the fork is kept taut at all times as a result of various special expedients including a differential spool and drum and a rack and pinion floss locking arrangement. When the supply of fresh floss on the bobbin is exhausted, the device is discarded.

7 Claims, 2 Drawing Sheets

DENTAL FLOSSING DEVICE

BACKGROUND OF THE INVENTION

1. Field of the Invention

This invention relates generally to hand-held instruments for flossing teeth and, more particularly, to a self-contained article which, in the interests of enhancing oral hygiene, is easily and readily manipulated and provides a one-touch, floss-advancing arrangement so that a fresh section of tensioned floss is presented at each use.

2. Prior art.

A search revealed the following United States patents:

| | | |
|---|---|---|
| 553,610 | 3,746,017 | 4,460,002 |
| 1,306,998 | 3,927,687 | 4,706,694 |
| 1,640,607 | 4,051,857 | 4,790,336 |
| 2,187,442 | 4,094,328 | 4,807,651 |

Although the present dental flossing device and the prior art floss applicators share various features, it is believed that several of the features of the present device are patentably distinct over the prior art disclosures. Inclusive of such distinctive features, although not limited thereto, are the comfortable shape of the elongated handle to facilitate manipulation, and the one-touch, floss-advancing arrangement with automatic floss tensioner and tension lock.

SUMMARY OF THE INVENTION

An elongated handle fits comfortably and securely in the hands of the user; and on a neck on the forward end of the handle is mounted a U-shaped flossing head comprising a pair of tines, or legs. Inside the handle a supply of dental floss is pre-wound on a tapered bobbin, or spool. From the smaller diameter end of the bobbin the initial charge of floss extends through the neck to the base of the proximal tine, or leg, of the U-shaped flossing head, then up through the proximal leg to emerge from the tip thereof, thence across the space between the tips of the legs to enter the opposite tip and down the length of the distal tine, or leg. From the bottom of the distal leg the floss travels across the base of the U-shaped flossing head and emerges from the bottom of the proximal leg, thence through the neck to a coaxially mounted take-up reel having a cylindrical take-up drum.

Initial floss tension is maintained throughout owing to the fact that as subsequent charges of fresh floss are removed and the increasingly larger diameter of the tapered spool provides a greater length of floss for each angular arc of rotation of the bobbin and the take-up reel, the greater length of released floss is accommodated by the increasingly greater effective diameter of the take-up reel as spent floss accumulates on the drum of the take-up reel. The tension thereby established is locked in place by a transverse toothed arm on a spring-urged slide, the toothed arm engaging and thus immobilizing a pinion mounted coaxially with the bobbin and the take-up reel. Rotation of the bobbin and the take-up reel is effected by disengagement of the transverse toothed arm from the pinion and engagement with the pinion of a rack on the adjacent lower surface of an actuator slidably mounted on the handle and urged against spring bias by force exerted by the user's thumb against a button projecting from the actuator.

BRIEF DESCRIPTION OF THE DRAWING FIGURES

DETAILED DESCRIPTION

Figure 1:
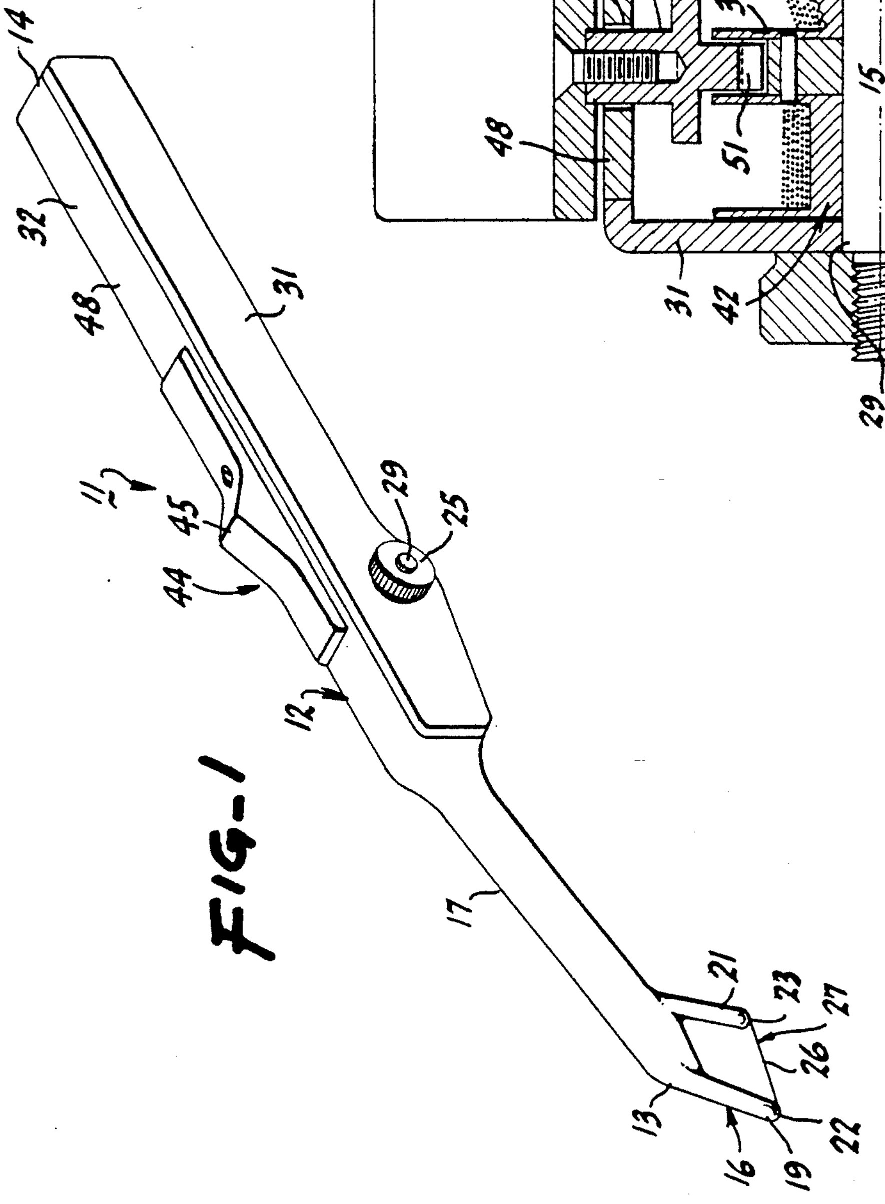
FIG. 1 is a perspective view of a dental flossing device constructed pursuant to the present invention.

The dental flossing device of the invention, generally designated by the reference numeral 11, includes an elongated, at least partially hollow handle 12 of generally rectangular in cross-sectional shape to afford a secure yet comfortable grip. The handle extends from a forward end 13 to an after end 14 and carries on the forward end 13 a flossing head 16 and neck 17.

The flossing head 16 comprises a U-shaped fork 18 having a pair of tines, namely, a forward tine 19 and an after tine 21.

Spanning the tip 22 of the forward tine 19 and the tip 23 of the after tine 21 is a tightly tensioned section 26 of fresh, unused floss 27.

The fresh floss 27 is supplied from a bobbin 28 rotatably mounted on an axle 29 spanning the opposite side walls 31 and 32 of the handle 12.

Figure 5:
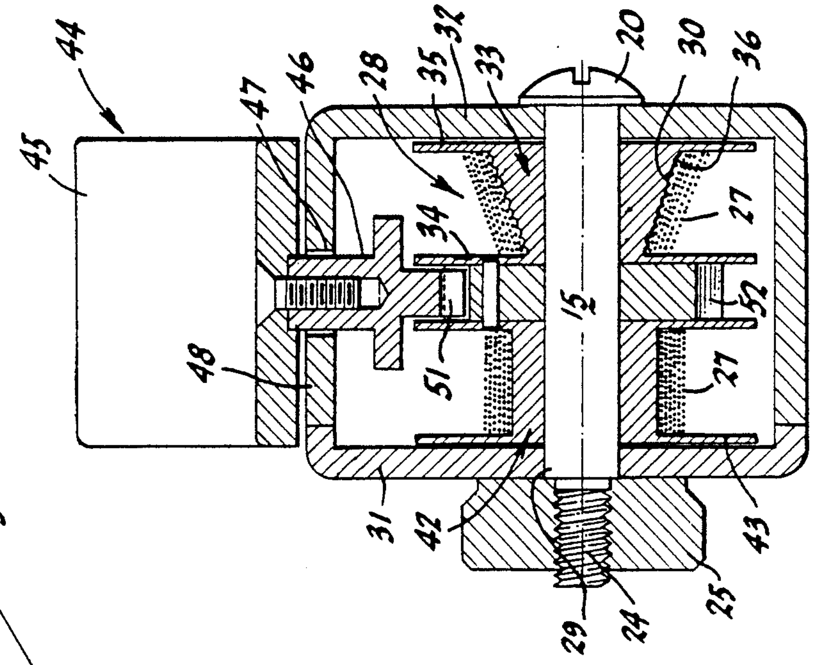
FIG. 5 is a transverse sectional view, to an enlarged scale, taken on the line 5—5 in FIG. 3.

Conveniently, the axle 29 can be the smooth elongated shank of a modified bolt 15 having at one end a head 20 and, at the other end, a threaded portion 24 engageable by a nut 25 which bears, in closed position, as in FIG. 5, against the adjacent side wall 31. In other words, after the bobbin 28 and floss 27 are put in place at the factory, the side wall 31 is arranged in mating position and the nut 25 is threaded into closed position, as shown in FIG. 5. Alternate closing arrangements for the side 31 include any conventional snap-lock, or interference type of fit or by closing with an adhesive.

The bobbin 28 is unique in that it includes a spool 33 that is tapered from a relatively small diameter adjacent an inner end flange 34 to a relatively large diameter adjacent an outer end flange 35.

The surface 30 of the tapered spool 33 is treated so that fresh floss 27 initially wound on the spool does not shift laterally, but, rather, securely remains in initial position.

The surface 30 of the tapered spool 33 can be rough, or it can be indented with a plurality of small parallel peripheral grooves 36, for example, adapted to receive and securely maintain the initial placement of the floss as it feeds out and progressively reels off floss from the smaller diameter end of the tapered spool 33 toward the larger diameter end thereof.

From the bobbin 28, the floss extends forwardly through a first bore 37 in the neck 17 and head 16, thence through a second bore 38 in the forward tine 19, emerging therefrom at the tip 22.

The fresh floss 27 spans the tips of the tines, across the section 26, and enters the tip 23 of the after tine 21, extending through a third bore 39, a fourth bore 40 and, lastly, a fifth bore 41.

At the after end of the fifth bore 41, the spent floss 27 emerges from the bore and is wound on the right circular-cylindrical drum 42 of a take-up reel 43 coaxially mounted and movable in unison with the bobbin 28 about the axis of the axle 29.

The diameter of the drum 42 is substantially identical to the smaller diameter of the tapered spool 33 of the bobbin 28. Thus, the initial charges of floss, feeding from the small diameter end of the tapered spool 33, and rewinding on the cylindrical drum 42, maintain the initial tension established on the floss at the time of manufacture. The spent floss, in other words, initially winds onto the exposed drum 42 as fast as the fresh floss unwinds off the small diameter end of the tapered spool 33.

The static friction between the walls of the various bores 37–41 and the floss assists, also, in maintaining the tension in the floss section 26 so that the user will, even at the start, have available a tight, unobstructed length of floss, thereby enhancing the effectiveness of the device as an instrument for oral hygiene.

As succeeding charges of floss unwind from the bobbin 28 and extend through the path defined by the bores 37–41 to rewind on the take-up reel 43 as spent floss, the floss leaves the tapered spool 33 from areas of increasingly larger diameter. In other words, each angle of rotational arc of the bobbin results in the release of a greater length of fresh floss as the larger spool diameters are reached. At the same time, however, the spent floss has been building up to a larger outer diameter on the cylindrical drum 42 of the take-up reel 43. Thus, the two rotating members, moving in unison, balance the fresh floss movement with the spent floss movement and tension is maintained across the floss section 26 at all times.

In order to advance the fresh floss and re-wind the spent floss, a special actuator 44 is provided.

Figures 2, 3, 4:
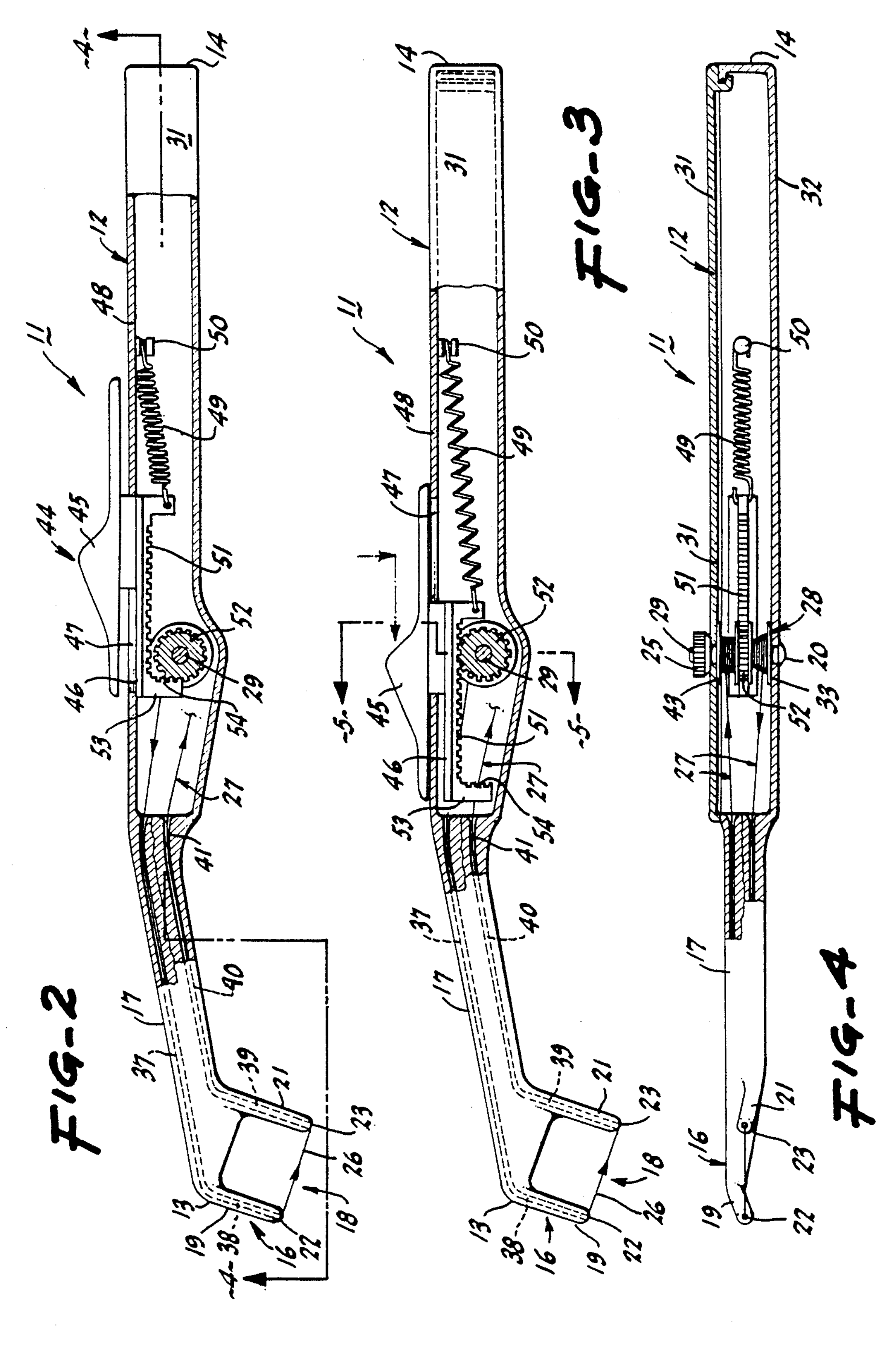
FIG. 2 is a longitudinal view partially in section, showing the actuator slide in its base or fully-retracted, pinion-locking position.
FIG. 3 is a view similar to FIG. 2 but with the actuator slide in fully extended position at the end of its pinion-rotating and floss-advancing stroke.
FIG. 4 is a longitudinal sectional view, taken on the line 4—4 in FIG. 2.

The actuator 44 includes a boss 45, or button, or lever, projecting upwardly from a slide 46, the boss 45 being attached to the slide 46 so that as the user's thumb engages the boss 45 and urges the boss in a forward direction from the fully retracted position shown in FIG. 2 to the fully extended position shown in FIG. 3, the slide 46 partakes of the same motion.

Accurate fore and aft motion of the boss 45 and the slide 46 is attained by providing a fore and aft slot 47 in the top wall 48 of the handle 12. The slide 46 is translatable in the slot 47 between the fully retracted and fully extended positions, as shown.

The after end of the slide 46 is connected to a helical tension spring 49 secured to a bracket 50 on the inner surface of the top wall 48 at a location such that the axis of the helical spring 49 is slightly inclined to the longitudinal, fore and aft axis of the handle 12, so as to provide an upward component of urgency on the slide 46 and the boss 45, tending to urge the slide 46 and the boss 45 upwardly as well as rearwardly, into the base, or fully retracted, position shown in FIG. 2.

When actuating the slide 46 so as to advance the fresh floss in a new charge, the user's thumb not only pushes forwardly on the boss 45 but also pushes downwardly on it to a small extent, thereby overcoming the rearward and slight upward urgency exerted by the spring 49.

By pushing somewhat downwardly on the boss 45 and the slide 46, a rack 51, comprising a series of small teeth formed in the bottom of the slide 46, engages a pinion 52, integral with and located between the bobbin 28 and the take-up reel 43 and in coaxial relation therewith. Thus, as the rack teeth are urged forwardly in engagement with the pinion teeth, the rack teeth rotate the bobbin 28 and the take-up reel 43 as well as the pinion 52.

The pinion is preferably interposed, as shown, between the bobbin 28 and the take-up reel 43 in order physically to separate the fresh floss supply from the spent floss reel, for sanitary reasons.

The forward, or floss-advancing stroke is halted as the slide 46 encounters the forward end of the slot 47 in the top wall 48 of the handle. This marks the fully extended position shown in FIG. 3, at which juncture the taut, fresh floss section 26 has been renewed, ready for use as soon as the user's thumb is released from engagement with the boss 45 and the spring 49 has had time to lift and disengage the slide rack 51 from the pinion 52 and to return the actuator 44 to base, or inactive, or fully retracted position, as illustrated in FIG. 2.

As a final, unique, tension-maintaining feature, the forward end of the slide 46 is provided with a transverse arm 53 which, in itself, is a linear rack in that the after surface of the arm is provided with teeth 54 adapted to engage the teeth of the pinion 52 in base or fully retracted position of the actuator 44. Thus, in the fully retracted position, as appears most clearly in FIG. 2, the arm teeth 54 engage and totally immobilize, or lock, the pinion 52, the bobbin 28 and the take-up reel 43, thereby positively maintaining the tension on the floss and precluding over dispensing of fresh floss from the bobbin 28.

What is claimed is:

1. A dental flossing device comprising:

a. an elongated handle extending from a forward end to an after end;

b. a fork having a pair of elongated tines, said fork being mounted on said forward end of said handle;

c. a bobbin containing a supply of dental flosses, said bobbin being rotatably mounted on said handle to supply a predetermined amount of floss across the tip ends of said tines, said bobbin including a pair of annular end flanges and an intermediate spool portion, said spool portion being tapered in profile and increasing in diameter as said spool portion extends from one of said annular end flanges toward the other of said annular end flanges so that identical angular rotation of said bobbin releases a greater linear amount of floss from the large diameter end of said spool portion than from the small diameter end thereof;

d. a take-up reel rotatably mounted on said handle to receive spent floss from said tines, said take-up reel and said bobbin being rotatable on a common axis, said take-up reel including a pair of annular end walls and an intermediate drum portion of substantially uniform diameter so that as spent floss builds up on said drum portion, identical angular rotation of said take-up reel retrieves a progressively greater linear amount of floss from said bobbin;

e. means mounted on said handle for advancing a predetermined amount of floss from said bobbin across said tines and to said take-up reel; and, f. means for selectively locking said bobbin and said take-up reel when said floss advancing means is inactive.

2. A device as in claim 1 in which the tapered profile of said spool portion maintains tension on the floss across said tines as said bobbin and said take-up reel are advanced an identical angular amount and fresh floss is released progressively from the smaller diameter end of said spool portion toward said larger diameter end thereof as spent floss is progressively retrieved on said drum and builds up thereon.

3. A device as in claim 2 in which said spool portion is surface treated to hold the floss supply in its originally wound position.

4. A device as in claim 1 in which said floss advancing means includes an elongated slide translatably mounted on said handle for fore and aft movement thereon, said slide having a boss protruding outwardly from said handle, a pinion disposed coaxially with said bobbin and said take-up reel and being rotatable therewith, and a rack mounted on said slide and engageable with said pinion, for rotating said pinion, said bobbin and said take-up reel in unison as said boss and said slide are urged from a first position toward a second position parallel to the longitudinal axis of said handle.

5. A device as in claim 4 including means for disengaging said rack from said pinion as said boss and said slide move from said second toward said first position.

6. A device as in claim 5 including a toothed arm mounted on said slide for engagement with said pinion in said first position of said slide and said boss.

7. A device as in claim 6 in which said rack disengaging means includes a helical spring mounted on said handle and on said slide with the longitudinal axis of the spring inclined to afford a lateral component urging said rack away from said pinion.

* * * * *